(12) United States Patent
Potze et al.

(10) Patent No.: US 11,337,619 B2
(45) Date of Patent: May 24, 2022

(54) DETECTION OF METAL ARTIFACTS IN PATIENTS EYES PRIOR TO MRI EXAMINATIONS

(71) Applicant: KONINKLIJKE PHILIPS N.V., Eindhoven (NL)

(72) Inventors: Willem Potze, Geldrop (NL); Petrus Carolus Maria Frissen, Beek (NL); Aditya Mehendale, Geldrop (NL); Jacek Lukasz Kustra, Eindhoven (NL); Peter Prinsen, Eindhoven (NL); Guillaume Leopold Theodorus Frederik Hautvast, Veldhoven (NL)

(73) Assignee: Koninklije Philips N.V., Eindhoven (NL)

( * ) Notice: Subject to any disclaimer, the term of this patent is extended or adjusted under 35 U.S.C. 154(b) by 601 days.

(21) Appl. No.: 16/319,966

(22) PCT Filed: Aug. 2, 2017

(86) PCT No.: PCT/EP2017/069537
§ 371 (c)(1),
(2) Date: Jan. 23, 2019

(87) PCT Pub. No.: WO2018/024773
PCT Pub. Date: Feb. 8, 2018

(65) Prior Publication Data
US 2019/0261887 A1    Aug. 29, 2019

Related U.S. Application Data

(60) Provisional application No. 62/369,784, filed on Aug. 2, 2016.

(51) Int. Cl.
*A61B 5/06* (2006.01)
*A61B 5/00* (2006.01)
(Continued)

(52) U.S. Cl.
CPC .............. *A61B 5/062* (2013.01); *A61B 5/055* (2013.01); *A61B 5/6821* (2013.01);
(Continued)

(58) Field of Classification Search
CPC . A61B 5/062; A61B 5/6821; A61B 2562/182; G01R 33/288; G01V 3/10
See application file for complete search history.

(56) References Cited

U.S. PATENT DOCUMENTS 4,526,177 A   7/1985  Rudy et al.
6,418,335 B2  7/2002  Arvin et al.
(Continued)

FOREIGN PATENT DOCUMENTS

CN    104749639 A    7/2015
JP      03218490 A    1/1990
JP    2012029972 A    8/2010

OTHER PUBLICATIONS

"Contactless Detection of Magnetic and Nonmagnetic Intraocular Foreign Bodies" by Urmakher et al. Biomed Eng 3, pp. 261-263 (Year: 1969).*
(Continued)

*Primary Examiner* — Jason M Ip

(57) ABSTRACT

A device (10) configured to detect the presence of metal artifacts in a patient's eye includes a head mount (14) configured to receive at least a portion of the patient's head. At least one inductor coil (12) is disposed on or in the head mount and positioned to inductively couple with at least one eye of the patient's head received into the head mount. An inductance meter (18) is operably connected to the at least one inductor coil to measure an inductance as a change of frequency of the at least one inductor coil. A processor (22) is programmed to: determine whether the inductance is greater than an inductance threshold value; and generate an indication of at least one metal artifact when the inductance
(Continued)

is greater than the inductance threshold value. A display component (24) is configured to display the indication.

15 Claims, 3 Drawing Sheets

(51) Int. Cl.
  *G01V 3/10* (2006.01)
  *A61B 5/055* (2006.01)
  *G01R 33/28* (2006.01)

(52) U.S. Cl.
  CPC ............ *A61B 5/6835* (2013.01); *A61B 5/742* (2013.01); *G01R 33/288* (2013.01); *G01V 3/10* (2013.01); *A61B 2562/182* (2013.01)

(56) References Cited

U.S. PATENT DOCUMENTS

| 2002/0077537 | A1 | 6/2002 | Avrin et al. | |
|---|---|---|---|---|
| 2002/0115925 | A1* | 8/2002 | Avrin | G01V 3/08 |
| | | | | 600/407 |
| 2003/0083588 | A1 | 5/2003 | McClure et al. | |
| 2004/0263379 | A1 | 12/2004 | Keller | |
| 2007/0052411 | A1 | 3/2007 | McClure et al. | |
| 2013/0190599 | A1* | 7/2013 | Wyeth | A61B 5/0522 |
| | | | | 600/409 |
| 2015/0339421 | A1 | 11/2015 | Srinivasan | |
| 2016/0054153 | A1* | 2/2016 | Sun | G01D 5/2006 |
| | | | | 324/207.12 |

OTHER PUBLICATIONS

Blyme et al. "Ultrasonographic Detection of Foreign Bodies in Soft Tissue" Arch. Orthop Trauma Surg. (1990), vol. 110 p. 24-25.

Efficient Metal Detection and Inductive Sensor Monitoring in Sub-UA Deep Sleep Mode Silicon Labs White Paper (Apr. 7, 2016).

* cited by examiner

DETECTION OF METAL ARTIFACTS IN PATIENTS EYES PRIOR TO MRI EXAMINATIONS

CROSS REFERENCE TO RELATED APPLICATIONS

This application is a U.S. national phase application of International Application No. PCT/EP2017/069537, filed on Aug. 2, 2017, which claims the benefit of U.S. provisional Application Ser. No. 62/369,784 filed on Aug. 2, 2016 and is incorporated herein by reference.

FIELD

The following relates generally to the magnetic resonance (MR) imaging safety screening arts, MR imaging metal artifact screening arts, and the like.

BACKGROUND

Patients that are scheduled for a magnetic resonance imaging (MRI) examination and are in certain risk categories have to be screened for electrically conductive and magnetic objects (e.g. small metal objects) inside the body. For certain patients such as metal workers, such screening includes screening for metal splinters in the eyes. The magnetic field generated by the MRI equipment will exert a force on metal objects. This force on the object has to be counterbalanced by the contact force at the interface between the metal object and the surrounding tissue. If this contact force is smaller than the force on the object generated by the magnetic field, the object will move through the body and damage and/or destroy the surrounding tissue. Especially, electrically conductive and magnetic splinters in the eye can move into the brain with serious or even fatal consequences.

Alternatively, eddy currents may be generated in the electrically conductive and magnetic object by the high frequency alternating magnetic field. These eddy currents in the object cause a heat generation (energy dissipation) in the objects. This heat will be transferred away from the object to the surrounding tissue by conduction (and possibly convection). The occurring rise in temperature may damage and/or destroy the surrounding tissue. Especially, a temperature rise of splinters in the eye can damage and/or destroy the eye. Hence, a patient that has electrically conductive and/or magnetic objects inside the body can get injured if he/she undergoes an MRI examination.

Traditionally the patient has to undergo an examination with X-rays to detect possible electrically conductive and magnetic objects in the body. The exposure to X-rays should be as small as possible, as X-rays in general are harmful to human tissue. X-ray damage to the eyes is of particular concern. Having a cost effective examination method in which the use of X-rays is avoided would be very beneficial for the patient.

The following discloses new and improved systems and methods that address the above referenced issues, and others.

SUMMARY

In one disclosed aspect, a device configured to detect the presence of metal artifacts in a patient's eye includes a head mount configured to receive at least a portion of the patient's head. At least one inductor coil is disposed on or in the head mount and positioned to inductively couple with at least one eye of the patient's head received into the head mount. An inductance meter is operably connected to the at least one inductor coil to measure an inductance as a change of frequency of the at least one inductor coil. A processor is programmed to: determine whether the inductance is greater than an inductance threshold value; and generate an indication of at least one metal artifact when the inductance is greater than the inductance threshold value. A display component is configured to display the indication.

In another disclosed aspect, a method for detecting the presence of metal artifacts in a patient's eye includes: measuring an inductance of the patient's eye; and displaying an indication of detection of an eye splinter when the measured inductance is greater than a threshold inductance value.

In another disclosed aspect, a device configured to detect the presence of metal artifacts in a patient's eye includes first and second inductor coils. The first inductor coil is arranged to overlie a left eye of the patient and the second inductor coil is arranged to overlie a right eye of the patient. The first and second inductor coils are connected with a metal detector circuit. A display component is configured to display an indication of an eye splinter in response to an output of the metal detector circuit satisfying an eye splinter criterion.

One advantage resides in providing a device to detect metal artifacts in a patient's eye prior to an MRI examination of the patient.

Another advantage resides in providing such a device which does not expose the eyes to x-rays.

Another advantage resides in providing such a device compensated for the capacitance of the patient's eyes to determine the presence of metal artifacts in the eyes.

Another advantage resides in providing such a device with a magnetically permeable Faraday shield to block electrical fields while not conducting current loops and hence not blocking magnetic fields to allow inductance of the eyes to be accurately measured.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the invention.

DETAILED DESCRIPTION

Figure 1:
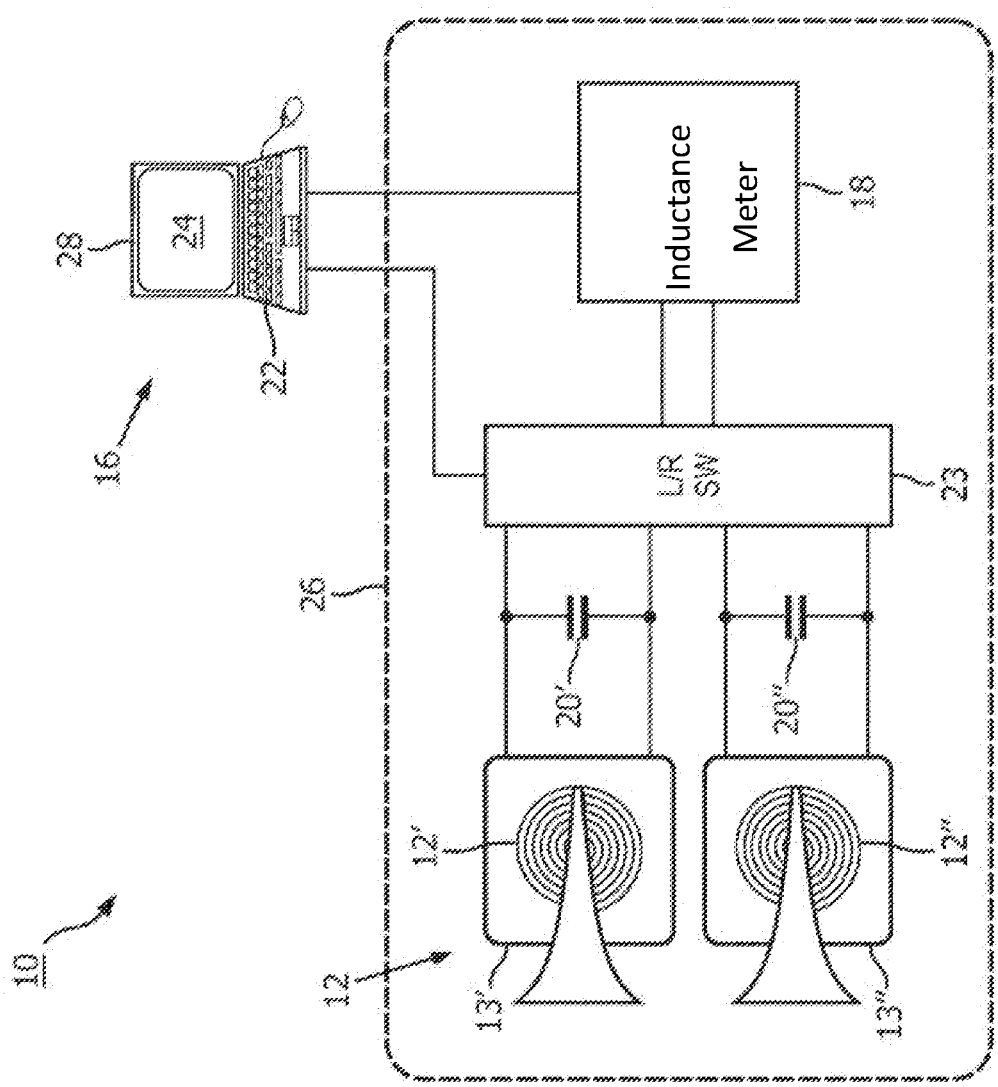
FIG. 1 schematically shows a device configured to detect the presence of metal artifacts in a patient's eye according to one aspect of the present disclosure.

An important part of patient safety screening for an MRI is assessing the patient for the presence of metal artifacts such as metal-containing prostheses. Another possible source of metal artifacts is metal splinters in the eye. While such an occurrence is relatively rare, it can be more common in certain classes of patients, such as welders or metal machine shop workers. Even a small splinter, on the order of 1 mm, can be hazardous as the MRI magnetic fields can move the splinter so as to damage the eye, or even move the splinter into the brain.

Conventionally, detection of metal splinters is performed as part of the overall safety screening process in which an x-ray scan is used to detect metal artifacts in the patient. If the patient is at risk for metal splinters in the eye, an additional x-ray head scan may be performed to detect any eye splinters. If an eye splinter is detected then the patient is not eligible for MRI (unless the splinter is surgically removed). The x-ray detection approach has the disadvantage of increased x-ray exposure to sensitive eye tissue.

Disclosed herein is a dedicated eye splinter detector device that employs an inductive metal detector. An inductor coil (or two coils in a binocular design) is arranged in a head mount to be held in a fixed position proximate to the eye. An Inductance-to-Digital Converter (LDC) is connected with the coil to measure inductance due to splinters.

To account for capacitance of the eye, a large capacitor may be placed in parallel with the inductive coil. In some embodiments, a capacitance that is at least 10-100 times larger than the eye capacitance seen by the coil may be used; more generally, the optimal capacitance value will depend on how much eye capacitance is seen by the particular coil configuration, which in turn depends on factors such as the eye-coil separation and the coil size/geometry.

The LDC is a commercially available component that typically energizes the coil at a programmed alternating-current (a.c.) frequency and detects the inductance. Some commercial LDCs provide for separate excite and receive coils. In general, a broad range of frequency may be used in the disclosed eye splinter screening device, e.g. in the range from tens of kHz into the MHz range in some embodiments. The frequency should be high enough to provide a detectable signal from the splinter of size 1 mm or so (splinters below about 0.1 mm are not expected to experience enough force during MRI to be hazardous). However, if the frequency is too high then eye capacitance can limit penetration depth and hence effectiveness in detecting splinters.

Optionally, a magnetically permeable Faraday cage may partially enclose the inductive coil and associated electronics. The Faraday cage may, for example, be constructed of interdigitated metal fingers to block electrical fields while not conducting current loops and hence not blocking magnetic fields.

Patients working in environments with metal splinters can actively be screened prior to an MRI examination. Traditionally in the screening method prior to an MRI examination X-rays are used to detect possible electrically conductive and magnetic objects in the body, especially in the eyes. In the proposed screening method, the traditional procedure of exposing the eyes of a patient to X-rays in order to detect eye splinters is avoided. The procedure is also less time-consuming, lower cost. Detection of an electrically conductive and magnetic eye splinter can be achieved by measuring inductance of the eye. By this technique, for example, only the presence of a splinter in the eye is detected and not the exact location. Non-ferrous metal eye splinters (e.g. aluminium) can also be detected, but with lower sensitivity. However, non-ferrous eye splinters do not experience MRI-induced force and will not move—they are only a risk for induced heating, and then only with larger-sized splinters capable of supporting substantial eddy currents. Accordingly, the lower sensitivity for non-ferrous eye splinters is acceptable. As the splinter is inside the eye, the capacitance of the environment (tissue) needs to be compensated. Small metal artifacts, typically the size of <1 mm$^3$, can be detected at distances of a few centimetres by the disclosed approach.

With reference to FIG. 1, a device 10 configured to detect the presence of metal artifacts in a patient's eye is schematically shown. The device 10 includes at least one inductor coil 12 configured to inductively couple with at least one eye of the patient. In some examples, the at least one inductor coil 12 includes first and second inductor coils 12', 12". The first inductor coil 12' is arranged to overlie one of the left or right eyes of the patient, and the second inductor coils 12" is arranged to overlie the other of the left or right eye of the patient. In some examples, the first and/or second inductor coils 12', 12" can be a spiral coil positioned overlaying the corresponding eye of the patient. In this example, a circular spiral generates a more symmetrical magnetic field, which provides the optimum shape from an inductance vs. resistance consideration. Thus, a circular inductor coil 12 is preferred for the highest possible sensing capabilities. In the illustrative embodiment, the first inductor coil 12' is a printed circuit on a first printed circuit board (PCB) 13' and likewise the second inductor coil 12" is a printed circuit on a second PCB 13". Such PCB-based spiral coils can be constructed inexpensively and with tight tolerances, and the planar nature of the PCB is convenient for placement proximate to an eye.

In some embodiments, the device 10 includes a head mount 14 (shown in FIG. 2) configured to receive at least a portion of the patient's head. The first and/or second inductor coils 12', 12" are disposed on a portion of the head mount 14 so that the inductor coils are positioned to inductively couple with a corresponding eye of the patient when the patient's head is received into the head mount.

Referring back to FIG. 1, the at least one inductor coil 12 is electrically connected with a metal detector circuit 16. The metal detector circuit 16 can include an inductance meter 18, a capacitance 20', 20" (one for each inductor 12', 12", forming respective LC tank circuits), and at least one processor 22. The inductance meter 18 is operably connected to the at least one inductor coil 12 to measure an inductance as a function of a change in frequency of the at least one inductor coil. In FIG. 1, the inductance meter 18 is electrically connected to either the first inductor coil 12' (or, to the first tank circuit 12', 20') or to the second inductor coil 12" (or, to the second tank circuit 12", 20") via a L/R switch 23 and configured to measure an inductance measurement output from the connected first or second inductor coil, as described in more detail below. For example, the inductance meter 18 can be a Inductance-to-Digital Converter (LDC) (available from Texas Instruments, Inc., Dallas, Tex.) connected with the at least one inductor coil 12 to measure inductance due to metal artifacts (i.e., splinters) in the eye of the patient. The L/R switch 23 enables separately screening: the left eye by connecting the first or left LC tank circuit 12', 20' to the inductance meter 18; and the right eye by connecting the second or right LC tank circuit 12", 20" to the inductance meter 18. In a variant embodiment (not shown), the two capacitances 20', 20" can be replaced by a single capacitance located between the inductance meter and the L/R switch, which reduces parts cost by eliminating one capacitor, but this circuit design is expected to provide less accurate results since it is advantageous to position the capacitance close to its corresponding inductor coil. In another variant embodiment, the L/R switch 23 is omitted in favor of providing separate first and second inductance meters, one for measuring each of the left and right LC tank circuits. This approach can provide simultaneous measurement of both left and right eyes, but at the cost of an additional part (the second inductance meter) which is a relatively expensive component.

In another variant embodiment (not shown), the L/R switch 23 can be omitted and the two inductor coils 12', 12" connected in series (so that the measured inductance is their sum) with the capacitance connected electrically in parallel across the inductor series. This arrangement provides simultaneous screening of both eyes. However, this arrangement does not permit discriminating which eye contains a detected metal artifact.

Figure 2:
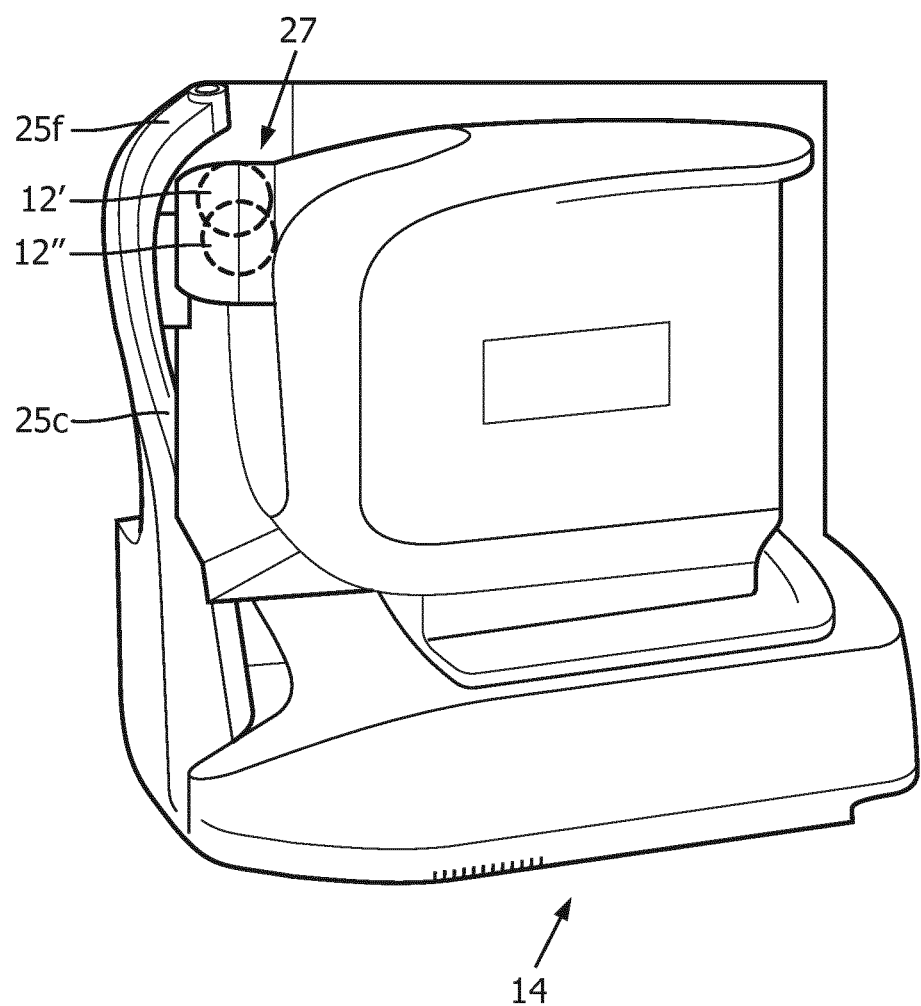
FIG. 2 shows a component of the device of FIG. 1.

The capacitance 20', 20" is connected electrically in parallel with the respective inductor coil 12', 12" to form an LC tank circuit. The capacitance is configured to account for capacitance of the screened eye (or eyes in the case of the embodiment employing a series connection of the left and right inductor coils) during the measurement of the inductor coil(s) 12. For example, the capacitance is at least 10 times greater than the capacitance of the eye (or eyes if using series-connected left and right inductor coils) as seen by the inductively coupled inductor coil 12. For example, the capacitance 20 can range from 300 picoFarads (pF) to 2 nF. In some examples, the inductance meter 18 comprises an inductance-to-digital converter (LDC) operating at an a.c. frequency controlled by the inductance and the capacitance 20 connected electrically in parallel with the at least one inductor coil 12. The inductance and capacitance determine the frequency of the at least one inductor coil 12. This relationship is based on Equation 1:

$$f = 1/2\pi\sqrt{LC} \qquad (1)$$

where f is the frequency of the at least one inductor coil 12, L is the inductance measured by the inductance meter 18, and C is the capacitance of the capacitance 20', 20". The frequency of the at least one inductor coil 12, can range from 1 kHz to 10 MHz. The frequency can change based on the position of the target. For example, if the at least one inductor coil 12 moves relative to the corresponding eye, the frequency of the at least one inductor coil 12 changes accordingly. To provide uniform positioning of each eye relative to its respective inductor coil 12', 12", the head mount 14 of FIG. 2 is preferably employed. For example, the illustrative head mount 14 includes a forehead rest 25f and chin rest 25c so that when the patient rests his or her forehead and chin against the respective rests 25f, 25c the eyes are properly positioned. Optional per-patient adjustments may be provided for the rests and/or a binocular assembly 27 containing the left and right inductor coils 12', 12". FIG. 2 is merely an illustrative example, and any other head mount configuration that provides acceptable head stabilization is suitable.

In some embodiments, the at least one processor 22 can be a computer processor (e.g., the at least one processor 22 is a component of a computer 28). For example, the at least one processor 22 is programmed to determine whether the inductance is greater than an inductance threshold value; and generate an indication of at least one metal artifact when the inductance is greater than the inductance threshold value. To do so, the at least one processor 22 is programmed to determine whether the induction measurement output is greater than an inductance threshold value by comparing the measured inductance value with a threshold inductance value. The induction measurement output is the induction output from the at least one inductor coil 12. The induction threshold value can range from approximately 0.5 picoHenrys (pH) to approximately 2.0 pH. For example, in some embodiments, the induction threshold value is approximately 1.0 pH, though the precise value for a given device depends on factors such as the size and inductance of the inductor coils 12', 12" and geometrical considerations such as the eye/coil spacing. In some examples, about 1.0 mm of conductor wire gives an inductance of approximately 1 nH. On the mechanical scale of the human eye, it does not make sense to expect to usefully resolve anything finer than 1 pH. The at least one processor 22 is then programmed to generate the indication of an eye splinter if the induction measurement output is greater than the induction threshold value. For example, the indication can be a series of light emitting diodes (LEDs) in which, for example, a red LED indicates the presence of one or more metal artifacts (i.e., a metal splinter) in the eye of the patient, while a green LED indicates the absence of metal artifacts in the eye. Additionally or alternatively, the indication could be a numerical value of the inductance, or an estimated splinter size computed based on the measured inductance translated into splinter mass and an assumed splinter material (e.g., steel). In another example, the indication can include a determination of which eye the splinter was found in. For example, a set of red and green LEDs can be included for each eye in the head mount 14. The green LED can be activated for either eye in which no splinter is found, while the red LED can be activated for either eye in which a splinter is found.

The device 10 can also include a display component 24 configured to display the indication. For example, the display component 24 can be configured to display the indication of an eye splinter in response to an output of the metal detector circuit 16 satisfying an eye splinter criterion (i.e., the presence of absence of metal artifacts in the patient's eyes). In some embodiments, the at least one processor 22 can be programmed to operate the display component to 24 generate the indication of an eye splinter if the induction measurement output is greater than the induction threshold value. For example, the indication can be a message of "splinter detected" or "no splinter detected" or equivalents thereof.

In embodiments such as those of FIG. 1 which permit separately measuring the left and right eyes, the measurement is repeated for each eye and any indication can be identified as to the eye in which the splinter was detected. This can be helpful for assisting medical professionals in performing an ophthalmological examination of the appropriate eye to assess (and treat, e.g. remove if appropriate) the metallic artifact. In the embodiment of FIG. 1, the measurements of the left and right eye are performed consecutively, but since they can be performed by operating the L/R switch 23 this can be done in rapid succession so that the patient perceives a single test of both eyes. It may be noted that the test does not involve emitting light into the eye(s), and hence appears entirely non-invasive to the patient.

In some embodiments, the device 10 can include a magnetically permeable Faraday cage 26 arranged to at least partially enclose the inductor coils 12', 12" and patient portion or all of the associated metal detector circuit 16. The diagrammatically illustrated Faraday cage 26 encloses the inductor coils 12', 12", the capacitances 20', 20", the L/R switch 23, and the inductance meter 18. To make the cage magnetically permeable, the Faraday cage 26 may, for example, be constructed of interdigitated metal fingers to block electrical fields while not conducting current loops and hence not blocking magnetic fields. Advantageously, inductance of the eyes can be measured by the inductance meter 18. In some examples, when the first and/or second inductor coils 12', 12" are present, the device 10 includes first and second magnetically permeable Faraday cages (not shown) each configured to at least partially enclose a corresponding one of the first and second inductor coils and a corresponding portion of its electronics. Alternatively, a single cage may enclose both elements, e.g. in the head mount 14 of FIG. 2 a single Faraday cage 26 may enclose the binocular assembly 27, with the inductor coils 12', 12", the capacitances 20', 20", the L/R switch 23, and the inductance meter 18 all installed inside the shielded binocular assembly 27.

Figure 3:
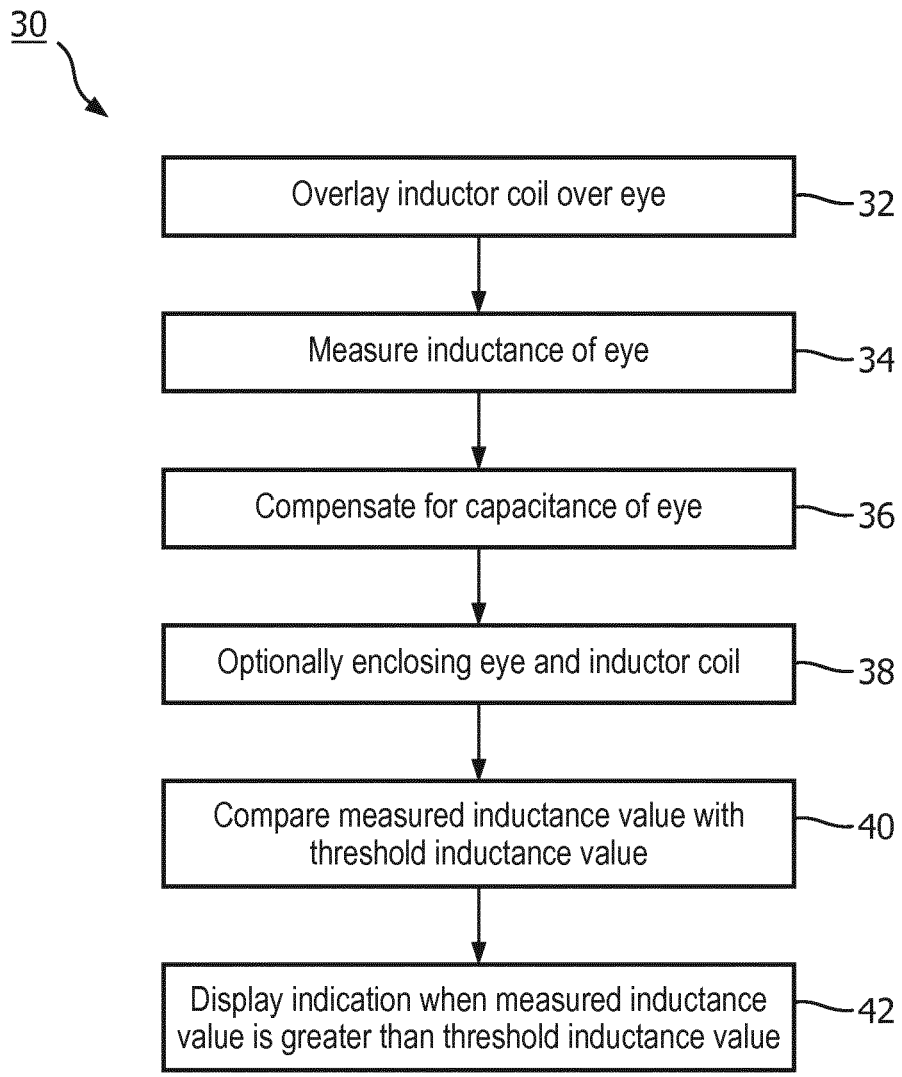
FIG. 3 shows an exemplary flow chart of an example operation of the device of FIG. 1.

FIG. 3 shows an exemplary flow chart of a method 30 of the operations of the device 10 for detecting the presence of metal artifacts in at least one eye of a patient. The method 30 includes: overlying at least one inductor coil 12 over at least one eye of a patient (step 32); measuring an inductance of at least one eye of a patient (step 34); during the measurement, compensating for a capacitance of the at least one eye of the patient via the capacitance 20' or the capacitance 20" (step 36); during the measurement, optionally electrically shielding the at least one inductor coil 12 and associated electronics via the Faraday cage 26 (step 38); comparing the measured inductance value with a threshold inductance value (step 40); and displaying an indication of detection of an eye splinter when the measured inductance is greater than the threshold inductance value (step 42). In the embodiment of FIG. 1, the steps 32, 34, 36, 38, 40 are repeated for each of the left and right eyes, and the step 42 may suitably display the results for both eyes.

In an illustrative more detailed example, in step 32, the at least one inductor coil 12 is overlaid over at least one eye of a patient. In one example, the at least one inductor coil 12 is disposed in the head mount 14 to overlie at least one eye of the patient. In another example, the first inductor coil 12' is overlaid over one of the left or right eyes of the patient, and the second inductor coil 12" is overlaid over the other of the left or right eye. The first and second inductor coils 12', 12" can be disposed in the head mount 14.

At 34, an inductance at least one of the patient's eyes is measured. To do so, an induction measurement output from the at least one inductor coil 12 is measured with the inductance meter 18 operably connected to the at least one inductor coil.

At 36, a capacitance of the at least one eye of the patient is compensated for. To do so, a capacitance of the at least one eye is measured with the at least one inductor coil 12. A capacitance of at least 10-100 times greater than the capacitance of the at least one eye measured by the at least one inductor coil 12 is generated with the at least one capacitance 20.

At 38, the at least one inductor coil 12 and the at least one eye of the patient are optionally enclosed. To do so, the at least one inductor coil 12 and the at least one eye are enclosed with the at least one magnetically permeable Faraday cage 26. In some examples, the first and second Faraday cages 26, 26" each configured to at least partially enclose a corresponding one of the first and second inductor coils 12', 12" and a corresponding one of the first and second eyes of the patient.

At 40, the measured inductance value is compared with a threshold inductance value. To do so, the at least one processor is programmed to compare the measured inductance value with the threshold inductance value. In one example, the induction threshold value is 1.0 pH. The at least one processor 22 is then programmed generate the indication of an eye splinter if the induction measurement output is greater than the induction threshold value. For example, the indication can be a series of light emitting diodes (LEDs) in which, for example, a red LED indicates the presence of one or more metal artifacts (i.e., a metal splinter) in the eye of the patient, while a green LED indicates the absence of metal artifacts in the eye.

At 42, an indication of detection of an eye splinter when the measured inductance is greater than the threshold inductance value is displayed. In some examples, the indication can be a message of "splinter detected" or "no splinter detected" or equivalents thereof, which can be displayed on the display component 24.

Referring back to FIG. 1, the device 10 can include components known in the art of metal detecting and computer systems. In one example, the device 10, the inductance meter 18, the at least one processor 22, and the display component 24 each include a memory. As used herein, a memory includes one or more of a non-transitory computer readable medium; a magnetic disk or other magnetic storage medium; an optical disk or other optical storage medium; a random access memory (RAM), read-only memory (ROM), or other electronic memory device or chip or set of operatively interconnected chips. As used herein, the device 10 can include a communication network (not shown) that includes an Internet/Intranet server from which the stored instructions may be retrieved via the Internet/Intranet or a local area network; or so forth. Further, as used herein, the at least one processor 22 includes one or more of a microprocessor, a microcontroller, a graphic processing unit (GPU), an application-specific integrated circuit (ASIC), a field-programmable gate array (FPGA), and the like. In a further example, a computer (not shown) can be provided which includes a user input device that includes one or more of a mouse, a keyboard, a touch screen display, one or more buttons, one or more switches, one or more toggles, and the like. In another example, the computer can include databases with one or more memories. In a further example, the display component 24 includes one or more of an LCD display, an LED display, a plasma display, a projection display, a touch screen display, and the like, including 3D-capable versions of these. In a further example, the device 10, the inductance meter 18, the at least one processor 22, and the display component 24 each include a communication unit and/or at least one system bus. The communication unit provides a corresponding processor with an interface to at least one communication network, such as a wireless network. The system bus allows the exchange of data between sub-components of the components. Subcomponents include processors, memories, sensors, display devices, communication units, and so on. In addition, the at least one processor 30 can comprise one or multiple processors.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A device configured to detect the presence of metal artifacts in a patient's eye, the device comprising:
   a head mount configured to receive at least a portion of the patient's head;
   at least one inductor coil disposed on or in the head mount and positioned to inductively couple with at least one eye of the patient's head received into the head mount;
   an inductance meter operably connected to the at least one inductor coil to measure an inductance as a change of frequency of the at least one inductor coil, the inductance meter comprising an inductance-to-digital converter (LDC) operating at an a.c. frequency controlled by the inductance and a capacitance connected electrically in parallel with the at least one inductor coil, the inductance meter being;

a processor programmed to:
  determine whether the inductance is greater than an inductance threshold value; and
  generate an indication of at least one metal artifact when the inductance is greater than the inductance threshold value; and a display component configured to display the indication.

2. The device of claim 1, wherein the inductor coil is a circular printed circuit board (PCB) spiral coil positioned overlaying one eye.

3. The device of claim 2, wherein the induction threshold value ranges from 0.5 pH to 2.0 pH.

4. The device of claim 1, wherein the capacitance is connected electrically in parallel with the at least one inductor coil to form an LC tank circuit.

5. The device of claim 4, wherein the capacitance connected electrically in parallel with the at least one inductor coil is at least 10 times greater than the capacitance of the at least one eye as measured by the inductance meter operably connected to the at least one inductor coil.

6. The device of claim 1, wherein the at least one inductor coil includes first and second inductor coils, the first inductor coil being configured to overlie a left eye of the patient and the second inductor coil being configured to overlie a right eye of the patient.

7. The device of claim 1, further comprising a magnetically permeable Faraday cage arranged to at least partially enclose the at least one inductor coil and the inductance meter.

8. A method for detecting the presence of metal artifacts in a patient's eye, the method comprising:
  positioning at least one inductor coil disposed on or in a head mount to overlie at least one eye of the patient;
  with an inductance meter operably connected to the at least one inductor coil, measuring an inductance measurement of the at least one inductor coil to measure an inductance of the patient's eye;
  with the at least one inductor coil, measuring a capacitance of the at least one eye;
  with at least one capacitance, generating a capacitance of at least 10-100 times greater than the capacitance of the at least one eye measured by the at least one inductor coil; and
  displaying an indication of detection of an eye splinter when the measured inductance is greater than a threshold inductance value.

9. The method of claim 8, wherein the induction threshold value ranges from 0.5 pH to 2.0 pH.

10. The method of claim 8, further comprising:
  overlying a first inductor coil over a first eye of the patient; and
  overlaying a second inductor coil over a second eye of the patient;
  wherein the measuring and displaying are performed for the first eye using the first inductor coil and for the second eye using the second inductor coil.

11. The method of claim 8, further comprising:
  with a magnetically permeable Faraday cage, enclosing the at least one inductor coil.

12. A device configured to detect the presence of metal artifacts in a patient's eye, the device comprising:
  first and second inductor coils, the first inductor coil arranged to overlie a left eye of the patient and the second inductor coil arranged to overlie a right eye of the patient, the first inductor coil positioned to inductively couple with the left eye of the patient, and the second inductor positioned to inductively couple with the right eye of the patient, wherein the first and second inductor coils are connected with a metal detector circuit comprising at least:
    an inductance meter operably connected to the first and second inductor coils and configured to measure an inductance measurement output from each of first and second inductor coils;
    a capacitance connected electrically in parallel with the inductor coils, the inductance meter comprising an inductance-to-digital converter (LDC) operating at an a.c. frequency controlled by the inductance and the capacitance connected electrically in parallel with the inductor coils; and
  a display component configured to display an indication of an eye splinter in response to an output of the metal detector circuit satisfying an eye splinter criterion.

13. The device of claim 12, wherein the metal detector circuit further includes:
  at least one processor programmed to:
    determine whether the inductance measurement output from either or both of the first or second inductor coils is greater than an inductance threshold value; and
    operate the display component to generate the indication of (i) an eye splinter in the left eye if the inductance measurement output from the first inductor coil is greater than the inductance threshold value and (ii) an eye splinter in the right eye if the inductance measurement output from the second inductor coil is greater than the inductance threshold value.

14. The device of claim 12, further comprising a head mount configured to receive a portion of the patient's head, the first and second inductor coils being disposed on the head mount.

15. The device of claim 12, further comprising magnetically permeable Faraday cage configured to at least partially enclose the first and second inductor coils and the inductance meter.

* * * * *